(12) United States Patent
Fumagalli et al.

(10) Patent No.: US 7,012,155 B2
(45) Date of Patent: Mar. 14, 2006

(54) PROCESS FOR THE PRODUCTION OF CARBOXYLIC ACIDS

(75) Inventors: Carlo Fumagalli, Albano Sant'Alessandro (IT); Francesco Minisci, Milan (IT); Roberto Pirola, Dalmine (IT)

(73) Assignee: Lonza S.p.A., Scanzorosciate (IT)

( * ) Notice: Subject to any disclaimer, the term of this patent is extended or adjusted under 35 U.S.C. 154(b) by 0 days.

(21) Appl. No.: 10/275,949

(22) PCT Filed: May 11, 2001

(86) PCT No.: PCT/EP01/05400

§ 371 (c)(1),
(2), (4) Date: Nov. 15, 2002

(87) PCT Pub. No.: WO01/87815

PCT Pub. Date: Nov. 22, 2001

(65) Prior Publication Data

US 2003/0144549 A1    Jul. 31, 2003

(51) Int. Cl.
C07C 51/31    (2006.01)
C07C 51/16    (2006.01)
C07C 51/245   (2006.01)

(52) U.S. Cl. ..................................... 562/527; 562/543
(58) Field of Classification Search ............... 562/527, 562/543
See application file for complete search history.

(56) References Cited

U.S. PATENT DOCUMENTS

| | | | |
|---|---|---|---|
| 2,223,493 A * | 12/1940 | Loder | 562/543 |
| 3,780,098 A   | 12/1973 | Morris | 562/528 |
| 4,146,730 A * | 3/1979  | Nishikido et al. | 562/543 |
| 4,902,827 A * | 2/1990  | Steinmetz et al. | 562/543 |
| 5,463,119 A * | 10/1995 | Kollar | 562/543 |

FOREIGN PATENT DOCUMENTS

| | | | |
|---|---|---|---|
| EP | 0694333 A1 | * | 5/1996 |
| FR | 2541993 | | 9/1984 |
| FR | 2791667 | | 10/2000 |
| GB | 415172 | * | 8/1934 |
| GB | 566110 | | 12/1944 |
| GB | 942415 | * | 11/1963 |
| GB | 1012237 | | 12/1965 |
| GB | 1026725 | | 4/1966 |

OTHER PUBLICATIONS

Grant et al , Grant& Hackh's Chem. Dict., McGraw-Hill Book Co., p. 56.*
Chemical Abstracts, vol. 71, No. 1, (Jul. 7, 1969), abstract No. 2982, (C.A. '982).
International Search Report from applicants' corresponding International (PCT) patent application.

* cited by examiner

*Primary Examiner*—Cecilia J. Tsang
*Assistant Examiner*—Taylor Victor Oh
(74) *Attorney, Agent, or Firm*—Fisher Christen & Sabol

(57) ABSTRACT

Aliphatic carboxylic acids of formulae (Ib) $R^1$—COOH(Ia) and $R^2$—COOH wherein $R^1$ is tertiary $C_{4-20}$-alkyl and $R^2$ together are —$(CH_2)_n$— with n=3 to 10, are produced by oxidizing an aliphatic or alicyclic ketone of the formula (II):

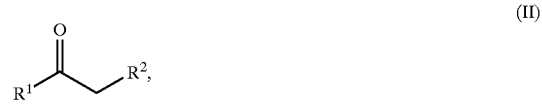

wherein $R^1$ and $R^2$ are as defined above, with molecular oxygen in the presence of a soluble manganese (II) compound. The process has a high selectivity and is carried out under very mild conditions. It is especially useful for the production of dicarboxylic acids, such as, adipic acid, from cyclic ketones.

17 Claims, No Drawings

PROCESS FOR THE PRODUCTION OF CARBOXYLIC ACIDS

This is a 371 of International (PCT) Application Number PCT/EP01/05400, filed on May 11, 2001, that has priority benefit of European Patent Application No. 00830350.5, filed on May 15, 2000.

The invention relates to a process for the production of carboxylic acids by the oxidation of aliphatic or alicyclic ketones.

Aliphatic carboxylic acids and their derivatives are compounds of particular industrial interest. In particular, dicarboxylic acids such as adipic acid, 1,8-octanedioic acid (suberic acid) or 1,12-dodecanedioic acid are valuable starting materials for the synthesis of polyamides and other polymeric materials.

Several syntheses of dicarboxylic acids starting from cyclic ketones are known in the art, some of them being performed on a commercial scale. The most commonly used oxidant is nitric acid, although some other oxidants have been investigated, too. The nitric acid oxidation has several drawbacks, resulting mainly from the corrosivity of nitric acid and the byproducts formed, in particular nitrous oxide which has been found to cause environmental problems.

The technical problem to be solved by the present invention was to provide a selective and high-yield process for the production of aliphatic carboxylic or dicarboxylic acids from aliphatic or cycloaliphatic ketones using a non-corrosive and environmentally friendly oxidant.

According to the present invention, this problem has been solved by the process of the invention.

It has been found that aliphatic carboxylic acids of the general formulae

   (Ia)

and

   (Ib)

wherein $R^1$ is tertiary $C_{4-20}$-alkyl
and $R^2$ is selected from hydrogen and $C_{1-6}$-alkyl,
or $R^1$ and $R^2$ together are —$(CH_2)_n$— with n=3 to 10,
can be prepared by oxidizing ketones of the general formula

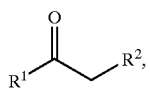   (II)

wherein $R^1$ and $R^2$ are as defined above, with molecular oxygen in the presence of a soluble manganese(II) compound.

Here and hereinbelow, $C_{1-6}$-alkyl is to be understood as any linear or branched primary, secondary or tertiary alkyl group having 1 to 6 carbon atoms, in particular groups such as methyl, ethyl, propyl, isopropyl, butyl, isobutyl, sec-butyl, tert-butyl, pentyl, neopentyl, hexyl and so on.

Tertiary $C_{4-20}$-alkyl is to be understood as any tertiary alkyl group having 4 to 20 carbon atoms, in particular groups such as tert-butyl(1,1-dimethylethyl) or tert-pentyl (1,1-di-methylpropyl).

The process according to the invention is applicable to the oxidation of open-chain (aliphatic) ketones as well as alicyclic ketones, the former yielding a pair of mono-carboxylic acids and the latter yielding a dicarboxylic acid.

In a preferred embodiment, $R^1$ and $R^2$ together are —$(CH_2)_n$— and n is an integer selected from 3, 4, 5, 6 and 10, corresponding to the alicyclic ketones cyclopentanone, cyclo-hexanone, cycloheptanone, cyclooctanone and cyclododecanone as starting materials and the dicarboxylic acids glutaric acid(1,5-pentanedioic acid), adipic acid(1,6-hexanedioic acid), pimelic acid(1,7-heptanedioic acid), suberic acid(1,8-octanedioic acid) and 1,12-dodecanedioic acid as products.

In another preferred embodiment, $R^1$ is tert-butyl and $R^2$ is hydrogen, the starting material being methyl tert-butyl ketone and the products (Ia) and (Ib) pivalic acid and formic acid, respectively.

Preferably, the soluble manganese(II) compound is manganese(II) nitrate. Other manganese(II) salts such as manganese(II) acetate may also be used.

More preferably, manganese(II) nitrate is used in an amount of 0.1 to 4 mol %, based on the amount of ketone (II).

The conversion rate and selectivity of the oxidation may be further improved by adding at least one compound selected from the group consisting of nitric acid, soluble cobalt(II) compounds and soluble copper(II) compounds in an amount of 0.1 to 5 mol %, based on the amount of ketone (II).

Preferably, the oxidation reaction is carried out in a solvent comprising at least one $C_{2-5}$-alkanoic acid. More preferably, acetic acid is used as solvent.

In a preferred embodiment, the molecular oxygen is used either in essentially pure form or in a gaseous mixture containing up to 90 vol % of nitrogen, e.g., ordinary air. Preferably, the total pressure is about 1 bar (i. e., ambient pressure) to 20 bar, more preferably about 1 bar to 5 bar.

The reaction temperature is preferably 0° C. to 100° C., more preferably 20° C. to 70° C. As the oxidation is exothermic, external cooling may be necessary to avoid thermal excursions.

Preferably, the oxidation reaction is carried out in a solvent, the weight ratio solvent/ketone being from 4 to 20 (i. e., 4:1 to 20:1). Besides the preferred alkanoic acids, any solvent which is essentially inert under the reaction conditions may be employed.

The invention is further illustrated by the following non-limiting examples.

EXAMPLE 1

Adipic Acid

A solution containing 25 mmol of cyclohexanone, 0.5 mmol of manganese(II) nitrate, 0.5 mmol of cobalt(II) nitrate and 1.5 mmol of nitric acid in 25 ml of acetic acid was stirred for 5 h at 40° C. in an oxygen atmosphere under ambient pressure. Subsequently, the acetic acid was distilled off. The residue was found to consist mainly of adipic acid with some glutaric acid and a small amount of unreacted starting material. The conversion of cyclo-hexanone was found to be 97.5%, the selectivity of the oxidation to adipic acid being 93.4%.

EXAMPLES 2–8

Comparative Examples 1–3

Adipic Acid

The procedure of Example 1 was repeated with different catalysts (without addition of nitric acid) at 20° C. or 40° C. The conditions and results are shown in Table 1.

TABLE 1

| Example No. | Catalyst [mmol] | Temperature [° C.] | Conversion [%] | Selectivity [%] |
|---|---|---|---|---|
| 2 | $Mn(NO_3)_2/0.5$ $Co(NO_3)_2/0.5$ | 20 | 68.7 | 92.2 |
| 3 | $Mn(NO_3)_2/0.5$ | 20 | 34.6 | 81.7 |
| 4 | $Mn(OAc)_2/0.5$ | 20 | 9.1 | 83.1 |
| 5 | $Mn(NO_3)_2/0.5$ $Co(NO_3)_2/0.5$ | 40 | 90.6 | 89.1 |
| 6 | $Mn(OAc)_2/0.5$ $Co(OAc)_2/0.5$ | 40 | 19.3 | 90.1 |
| 7 | $Mn(NO_3)_2/0.5$ $Cu(NO_3)_2/0.5$ | 40 | 91.6 | 89.5 |
| 8 | $Mn(OAc)_2/0.5$ $Cu(OAc)_2/0.5$ | 40 | 17.1 | 91.2 |
| C1 | $Co(NO_3)_2/0.5$ | 20 | 6.2 | 80.3 |
| C2 | $Co(OAc)_2/0.5$ | 20 | trace | — |
| C3 | $Cu(NO_3)_2/0.5$ | 20 | trace | — |

EXAMPLE 9

Adipic Acid

The procedure of Example 1 was repeated using 50 mmol of cyclohexanone instead of 25 mmol. The conversion of cyclohexanone was 95.7%, the selectivity 91.8%.

EXAMPLE 10

Adipic Acid

The procedure of Example 1 was repeated using air at 5 bar instead of oxygen at 1 bar. The conversion of cyclohexanone was 95.7%, the selectivity 92.6%.

EXAMPLES 11–14

The procedure of Example 1 was repeated using several different ketones as starting materials and a reaction temperature of 60° C. The results are compiled in Table 2.

TABLE 2

| Example No. | Ketone | Conversion [%] | Product | Selectivity [%] |
|---|---|---|---|---|
| 11 | Cyclopentanone | 98.2 | Glutaric acid | 91.7 |
| 12 | Cycloheptanone | 99.1 | Pimelic acid | 92.6 |
| 13 | Cyclooctanone | 97.8 | Suberic acid | 93.4 |
| 14 | Cyclododecanone | 98.6 | 1,12-Dodecane-dioic acid | 92.3 |

EXAMPLE 15

Pivalic Acid

The procedure of Example 1 was repeated using methyl tert-butyl ketone instead of cyclo-hexanone and 70° C. reaction temperature. The conversion was 89.6%, the selectivity 96.4%. Formic acid was formed as second product (Ib).

The invention claimed is:

1. A process for the production of aliphatic carboxylic acids of formulae:

$$R^1\text{—COOH} \quad (1a)$$

and $$R^2\text{—COOH} \quad (1b)$$

wherein $R^1$ is a tertiary $C_{4-20}$-alkyl
and $R^2$ is selected from hydrogen and $C_{1-16}$-alkyl, comprising oxidizing a ketone of formula:

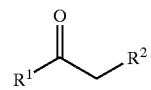

(II)

wherein $R^1$ and $R^2$ are as defined above,
with molecular oxygen in the presence of a soluble manganese(II) compound.

2. The process of claim, 1, wherein $R^1$ is tert-butyl and $R^2$ is hydrogen.

3. The process of claim 2, wherein the soluble manganese (II) compound is manganese(II) nitrate.

4. The process of claim 3, wherein the amount of manganese(II) nitrate is 0.1 to 4 mol percent with respect to the amount of ketone(II).

5. The process of claim 4, wherein the oxidation is carried out in a solvent comprising at least one $C_{2-5}$-alkanoic acid.

6. The process of claim 5, wherein the molecular oxygen is used in essentially pure form or in a gaseous mixture containing up to 90 vol percent of nitrogen, and total pressure is about 1 bar to 20 bar.

7. The process of claim 6, wherein reaction temperature is 0 to 100° C.

8. The process of claim 7, wherein a solvent is present in an amount corresponding to a weight ratio solvent/ketone of 4 to 20.

9. The process of claim 1, wherein the soluble manganese (II) compound is manganese(II) nitrate.

10. The process of claim 9, wherein the amount of manganese(II) nitrate is 0.1 to 4 mol percent with respect to the amount of ketone(II).

11. The process of claim 1, wherein the oxidation is carried out in a solvent comprising at least once $C_{2-5}$-alkanoic acid.

12. The process of claim 1, wherein molecular oxygen is used in essentially pure form or in a gaseous mixture containing up to 90 vol percent of nitrogen, and total pressure is about 1 bar to 20 bar.

13. The process of claim 1, wherein reaction temperature is 0 to 100° C.

14. The process of claim 13, wherein the reaction temperature is 20 to 70° C.

15. The process of claim 1, wherein a solvent is present in an amount corresponding to a weight ratio solvent/ketone of 4 to 20.

16. The process of claim 15, wherein reaction temperature is 20 to 70° C.

17. A process for the production of aliphatic carboxylic acids of formulae:

$$R^1\text{---COOH} \quad (1a)$$

and $$R^2\text{---COOH} \quad (1b)$$

wherein $R^1$ is a tertiary $C_{4\text{-}20}$-alkyl and $R^2$ is selected from hydrogen and $C_{1\text{-}16}$-alkyl, comprising oxidizing a ketone of formula:

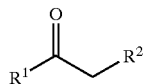
(II)

wherein $R^1$ and $R^2$ are as defined above, with molecular oxygen in the presence of a soluble manganese(II) compound, and in the present of at least one additive selected from the group consisting of nitric acid, soluble cobalt(II) compounds and soluble copper (II) compounds, in an amount of 0.1 to 5 mol percent with respect to the amount of ketone(II).

* * * * *